(12) United States Patent
Griffiths (10) Patent No.: US 9,636,178 B2
(45) Date of Patent: May 2, 2017

(54) SYSTEM AND METHOD FOR AN ARTICULATING SHAFT

(71) Applicant: Specialty Surgical Instrumentation Inc., Antioch, TN (US)

(72) Inventor: Jerry R. Griffiths, Norwell, MA (US)

(73) Assignee: Specialty Surgical Instrumentation, Inc., Antioch, TN (US)

( * ) Notice: Subject to any disclaimer, the term of this patent is extended or adjusted under 35 U.S.C. 154(b) by 611 days.

(21) Appl. No.: 13/705,262

(22) Filed: Dec. 5, 2012

(65) Prior Publication Data

US 2013/0150830 A1   Jun. 13, 2013

Related U.S. Application Data (60) Provisional application No. 61/567,891, filed on Dec. 7, 2011.

(51) Int. Cl.

| A61B 19/00 | (2006.01) |
|---|---|
| A61B 90/50 | (2016.01) |
| A61B 34/00 | (2016.01) |
| A61B 34/30 | (2016.01) |

(52) U.S. Cl.
CPC .............. *A61B 19/00* (2013.01); *A61B 90/50* (2016.02); *A61B 34/70* (2016.02); *A61B 2034/305* (2016.02)

(58) Field of Classification Search
CPC ......... A61B 19/26; A61B 19/22; A61B 19/00; A61B 2034/305; A61B 34/70; A61B 90/50
See application file for complete search history.

(56) References Cited

U.S. PATENT DOCUMENTS

| 4,662,815 | A | * | 5/1987 | Zimmer | ............... B25J 17/0283 |
| | | | | | 414/735 |
| 4,690,012 | A | * | 9/1987 | Dahlquist et al. | ......... 74/490.06 |
| 4,771,652 | A | * | 9/1988 | Zimmer | ............... B25J 17/0283 |
| | | | | | 74/469 |
| 4,990,050 | A | * | 2/1991 | Tsuge | ........................ B23Q 1/54 |
| | | | | | 414/735 |
| 5,540,706 | A | | 7/1996 | Aust et al. | |
| 5,761,965 | A | * | 6/1998 | Dahlquist | .................. 74/490.03 |
| 6,796,203 | B2 | * | 9/2004 | Dubrowskij | ............... 74/490.05 |
| 7,836,788 | B2 | * | 11/2010 | Kamon | ..................... B25J 9/06 |
| | | | | | 74/490.01 |

(Continued)

*Primary Examiner* — Gary Jackson
*Assistant Examiner* — Scott T Luan
(74) *Attorney, Agent, or Firm* — Hayes Soloway PC (57) ABSTRACT

An articulating shaft system includes an elongated shaft and first and second articulating components. The elongated shaft extends along a main axis and has a distal end surface that is not perpendicular to the main axis. The first articulating component is co-axial with the main axis and is positioned adjacent to the distal end surface of the elongated shaft and has a proximal end surface and a distal end surface that are not perpendicular to the main axis. The second articulating component is co-axial with the main axis and is positioned adjacent to the distal end surface of the first articulating component and has a proximal end surface that is not perpendicular to the main axis. Rotating the first articulating component around the main axis positions the first and second articulating components at an angle relative to the main axis.

20 Claims, 6 Drawing Sheets

(56) References Cited

U.S. PATENT DOCUMENTS

| | | |
|---|---|---|
| 2009/0125019 A1 | 5/2009 | Douglass et al. |
| 2010/0076461 A1 | 3/2010 | Viola et al. |
| 2010/0249497 A1* | 9/2010 | Peine et al. .................. 600/104 |
| 2011/0230875 A1 | 9/2011 | Walberg et al. |
| 2012/0116396 A1* | 5/2012 | Price et al. .................... 606/45 |

* cited by examiner

SYSTEM AND METHOD FOR AN ARTICULATING SHAFT

CROSS REFERENCE TO RELATED CO-PENDING APPLICATIONS

This application claims the benefit of U.S. provisional application Ser. No. 61/567,891 filed on Dec. 7, 2011 and entitled SYSTEM AND METHOD FOR AN ARTICULATING SHAFT which is commonly assigned and the contents of which are expressly incorporated herein by reference.

FIELD OF THE INVENTION

The present invention relates to a system and a method for an articulating shaft for a hand held device, and in particular, to an articulating multi-segment shaft that includes segments having ends that are not perpendicular to the main shaft axis.

BACKGROUND OF THE INVENTION

Medical instruments with articulating distal ends are used in various surgical procedures for inserting implants in a specific orientation or for accessing and grasping organs in a specific direction. Prior art systems usually include distal ends that articulate via a cable or an actuator rod system. Distal ends may be jaws, cutting blades, plates or rods, among others. In most of the prior art systems the articulating distal ends are not held rigid in their angular position. This may result in uncontrolled and imprecise movement of the implant or abrasion of the tissue or organ being grasped or injury of the surrounding tissue.

Accordingly there is a need for improved methods and systems that allow articulation of a distal end of a medical instrument while holding the distal end in a rigid position.

SUMMARY OF THE INVENTION

The present invention provides an articulating multi-segment shaft for a hand held device that includes segments having ends that are not perpendicular to the shaft main axis. The articulating shaft is used to change the orientation of a distal end device and to hold the distal end device in a rigid position.

In general, in one aspect, the invention features an articulating shaft system including an elongated shaft and first and second articulating components. The elongated shaft extends along a main axis and has a distal end surface that is not perpendicular to the main axis. The first articulating component is co-axial with the main axis and is positioned adjacent to the distal end surface of the elongated shaft and has a proximal end surface and a distal end surface that are not perpendicular to the main axis. The second articulating component is co-axial with the main axis and is positioned adjacent to the distal end surface of the first articulating component and has a proximal end surface that is not perpendicular to the main axis.

Implementations of this aspect of the invention may include one or more of the following features. The first articulating component is configured to rotate around the main axis and the rotation of the first articulating component around the main axis positions the first and second articulating components at an angle relative to the main axis. The elongated shaft includes an outer tubular component and an inner tubular component, and the inner tubular component is disposed within the outer tubular component and is configured to rotate around the main axis and to actuate rotational motion of the first articulating component. The outer tubular component has a distal end surface that is not perpendicular to the main axis. The proximal end surface of the first articulating component is co-planar with the distal end surface of the outer tubular component and the distal end surface of the first articulating component is coplanar with the proximal end surface of the second articulating component. The outer tubular component further includes first and second pins configured to connect the outer tubular component with the second articulating component. The second articulating component further includes a pin configured to align with and engage one of the first and second pins of the outer tubular component and thereby to provide a keyed joint between the outer tubular component and the second articulating component. The second articulating component includes first and second protrusions configured to connect to a removable distal end assembly.

In general, in another aspect, the invention features a method for articulating a distal end assembly including providing an elongated shaft, providing a first articulating component and providing a second articulating component. The elongated shaft extends along a main axis and has a distal end surface that is not perpendicular to the main axis. The first articulating component is co-axial with the main axis and is positioned adjacent to the distal end surface of the elongated shaft and has a proximal end surface and a distal end surface that are not perpendicular to the main axis. The second articulating component is co-axial with the main axis and is positioned adjacent to the distal end surface of the first articulating component and has a proximal end surface that is not perpendicular to the main axis. The method further includes attaching a distal end surface of the second articulating component to a distal end assembly and rotating the first articulating component around the main axis and thereby positioning the first and second articulating components and the distal end assembly at an angle relative to the main axis.

Among the advantages of this invention may be one or more of the following. The articulating shaft allows the distal end device to have controlled angular movement relative to the main shaft axis, while maintaining the distal end in a rigid position. The outer surface of the articulating shaft is sealed and does not include gaps.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

The present invention provides an articulating multi-segment shaft for a hand held device that includes segments having ends that are not perpendicular to the shaft main axis. The articulating shaft is used to change the orientation of a distal end device and to hold the distal end device in a rigid position.

Figure 1A:
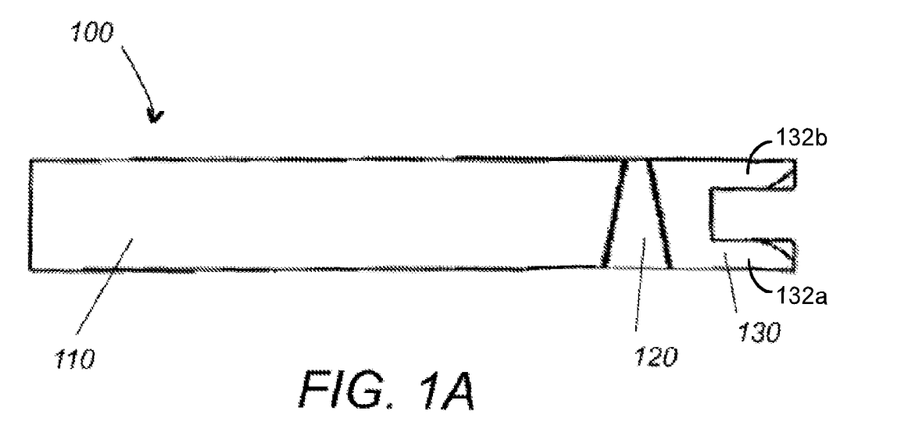
FIG. 1A is a side view of an articulating shaft according to this invention.
Figure 1B:
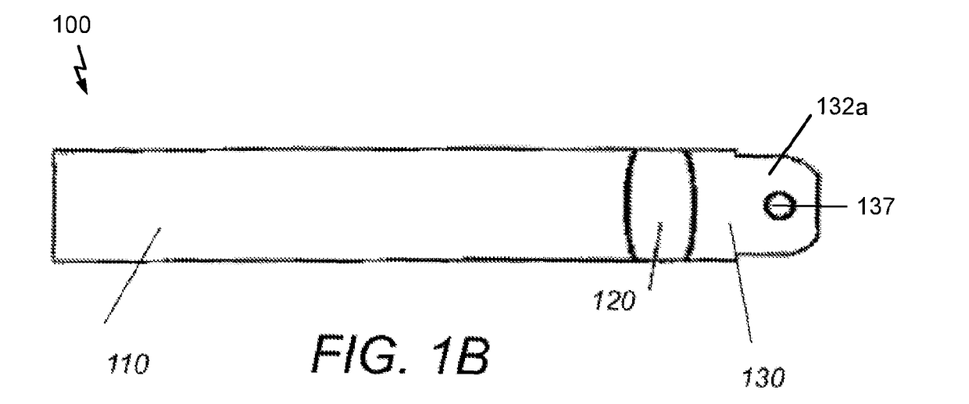
FIG. 1B is a bottom view of the articulating shaft of FIG. 1.
Figure 1C:
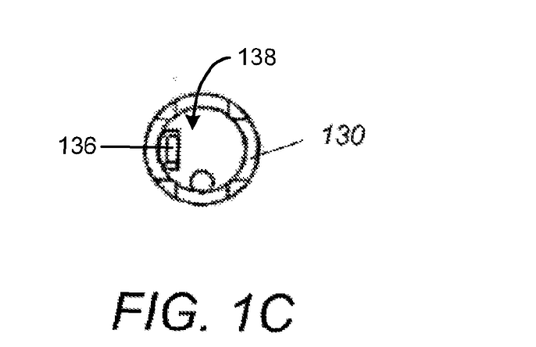
FIG. 1C is a front end view of the articulating shaft of FIG. 1.
Figure 4A:
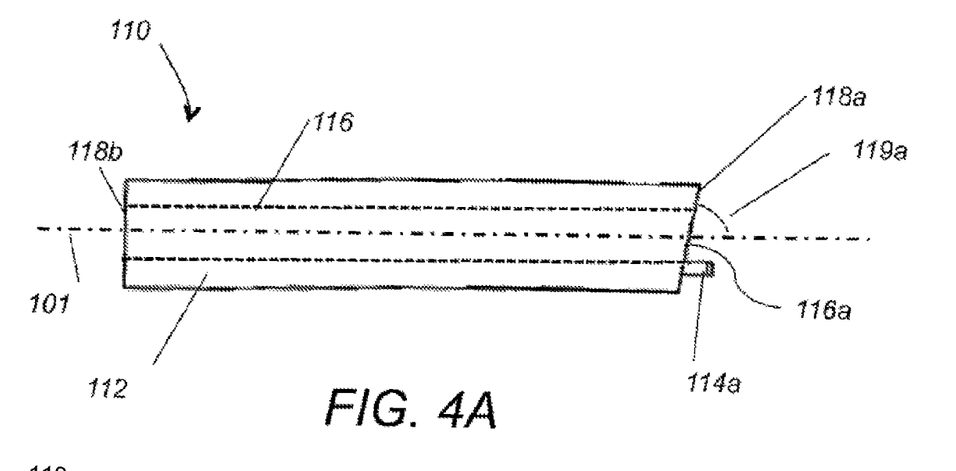
FIG. 4A is a side view of the first component of the articulating shaft of FIG. 1.
Figure 4B:
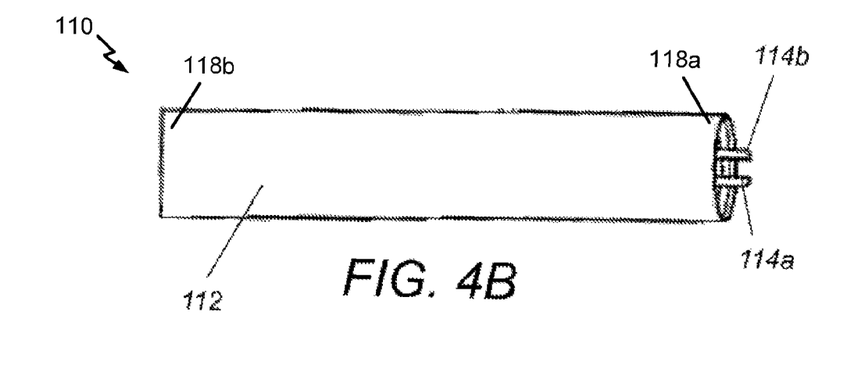
FIG. 4B is a bottom view of the first component of the articulating shaft of FIG. 1.
Figure 4C:
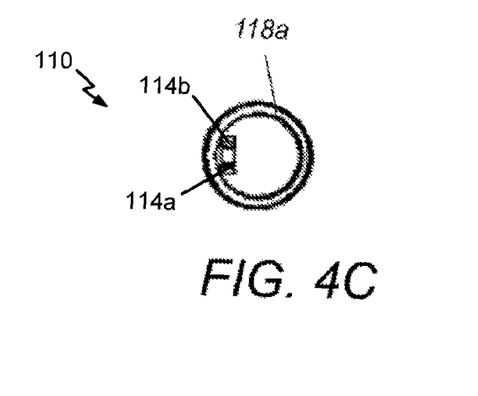
FIG. 4C is a front end view of the first component of the articulating shaft of FIG. 1.

Referring to FIG. 1, articulating shaft 100 includes first component 110, second component 120, and third component 130. First component 110 is positioned proximal to a tool handle (not shown) and includes an outer tubular elongated body 112 extending along axis 101 and an inner tube 116 disposed within tubular body 112, as shown in FIG. 4A. Inner tube 116 is used to actuate rotational motion of the second component 120 around axis 101 and thereby to position third component 130 at an angle 103 relative to axis 101, as shown in FIG. 2B and will be described below. Outer tubular body 112 includes a front distal end 118a and a rear proximal end 118b. The front distal end 118a of the outer tubular body 112 is cut at an angle 119a relative to axis 101, shown in FIG. 4A. Angle 119a is less or more than 90 degrees, which results in the plane of front distal end 118a not being perpendicular to the axis 101. First component 110 also includes pins 114a, 114b extending from the distal end 118a, as shown in FIG. 4A. Pins 114a, 114b are used to connect first component 110 to third component 130 in a certain orientation.

Figure 2A:
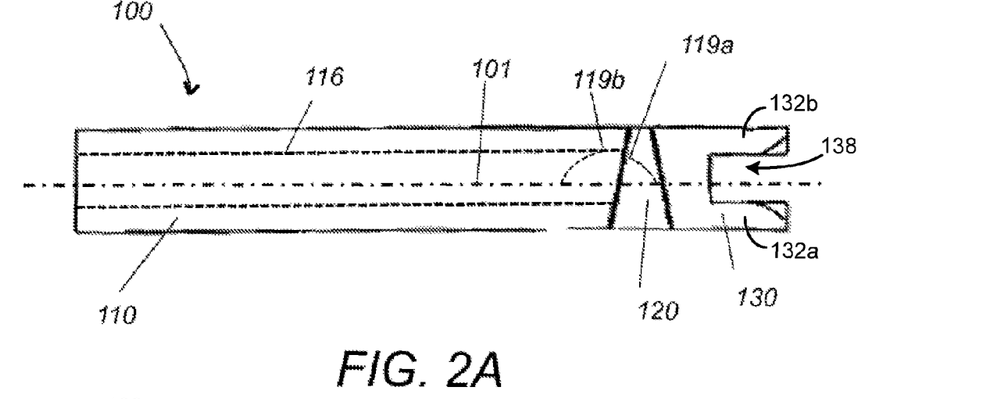
FIG. 2A is a side view of the articulating shaft of FIG. 1 in the straight orientation.
Figure 2B:
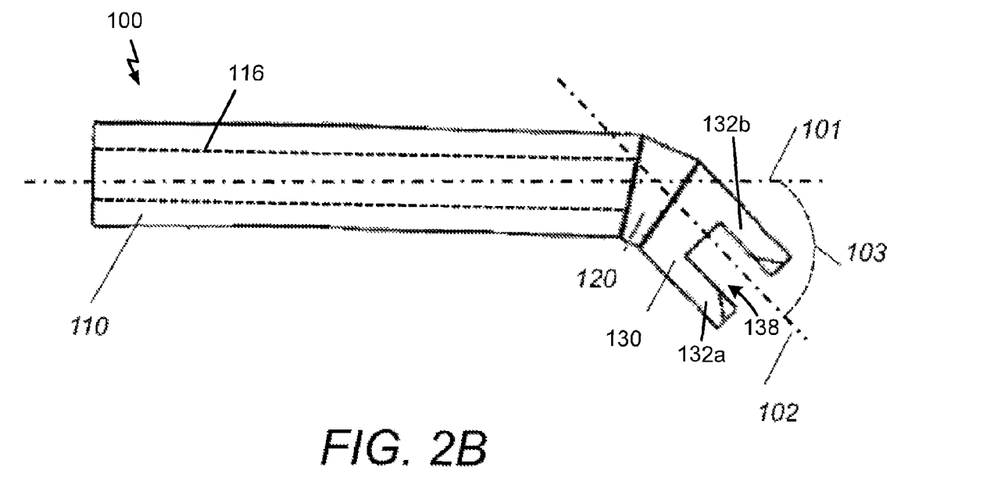
FIG. 2B is a side view of the articulating shaft of FIG. 1 in the articulated orientation.
Figure 3A:
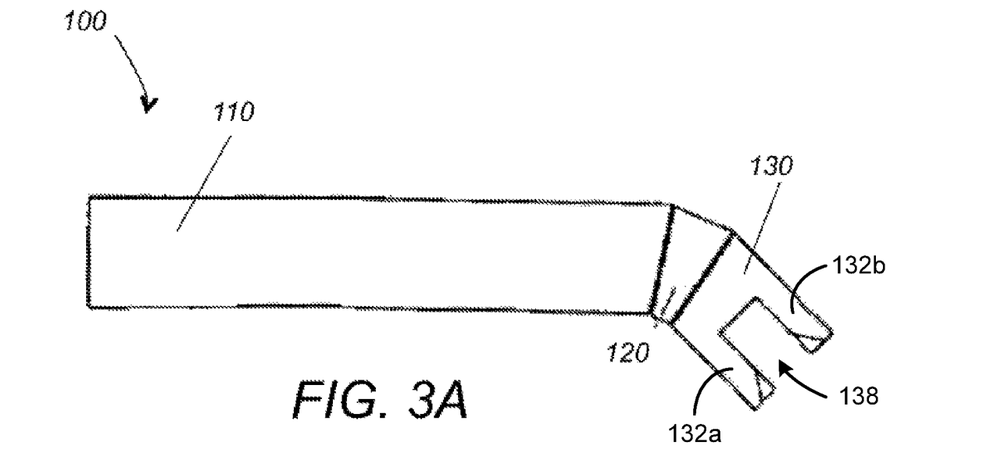
FIG. 3A is a side view of the articulating shaft of FIG. 1 in the articulated orientation.
Figure 3B:
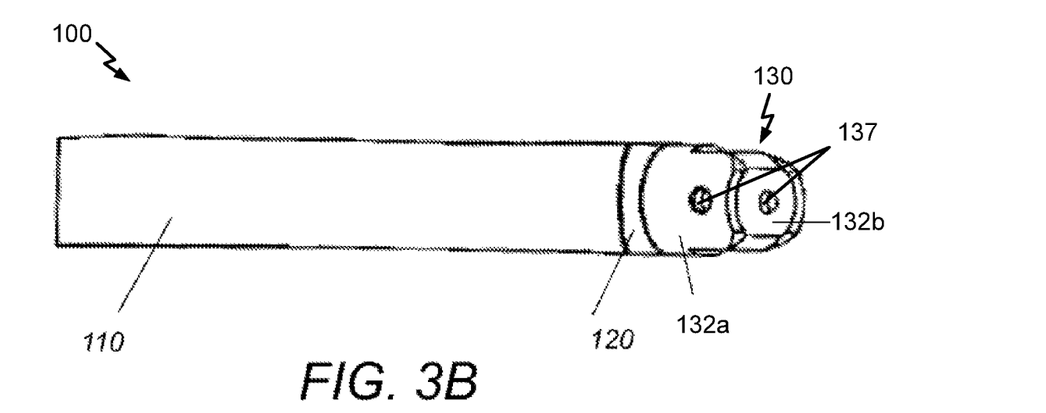
FIG. 3B is a bottom view of the articulating shaft of FIG. 1 in the articulated orientation.
Figure 3C:
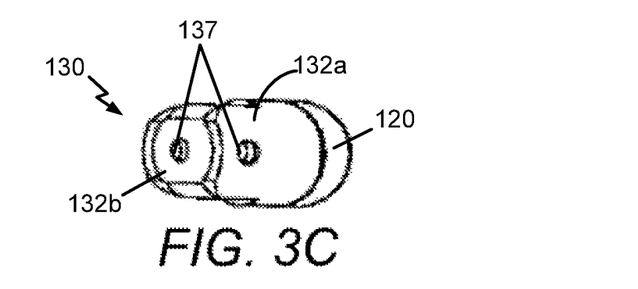
FIG. 3C is a front end view of the articulating shaft of FIG. 1 in the articulated orientation.
Figure 5A:
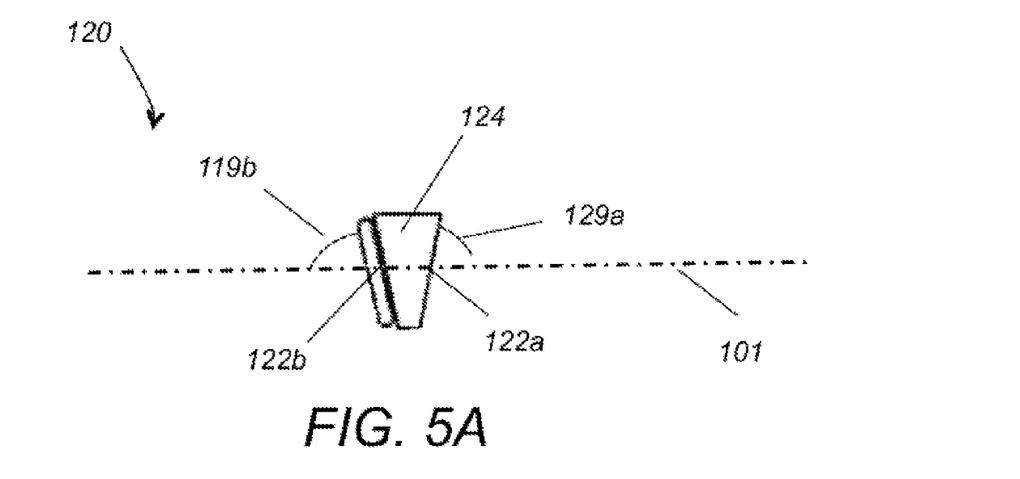
FIG. 5A is a side view of the second component of the articulating shaft of FIG. 1.
Figure 5B:
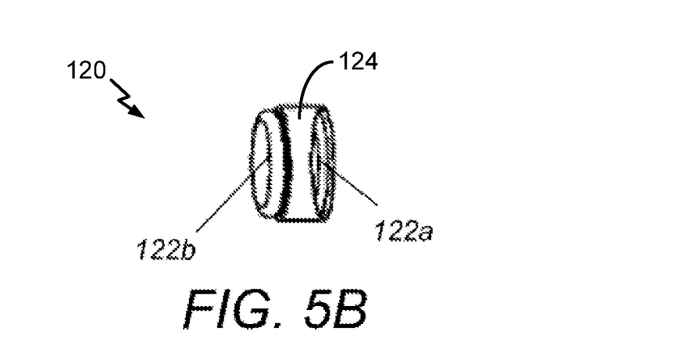
FIG. 5B is a bottom view of the second component of the articulating shaft of FIG. 1.
Figure 5C:
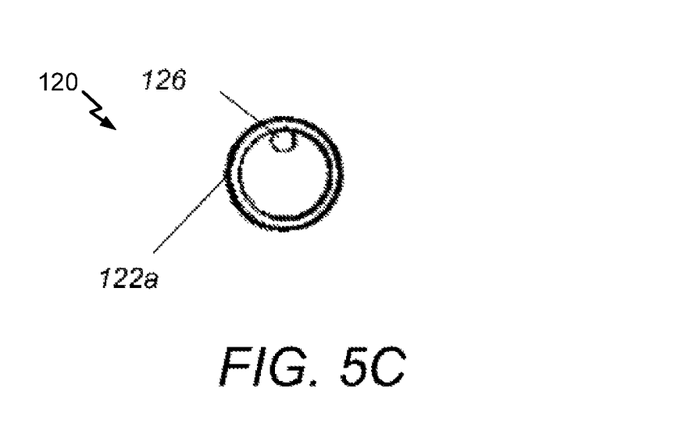
FIG. 5C is a front end view of the second component of the articulating shaft of FIG. 1.

Second component 120 is placed between first component 110 and third component 130 along axis 101, as shown in FIG. 2A. Second component 120 also includes a tubular body 124 that has a diameter equal to the diameter of the tubular body 112 of the first component 110, shown in FIG. 5A and FIG. 1A. Tubular body 124 has a proximal end 122b and a distal end 122a that are cut at angles 119b and 129a relative to axis 101, as shown in FIG. 5A. Angle 119b is supplementary to angle 119a of the first component 110, so that the plane of proximal end 122b aligns with the plane of front distal end 118a when the shaft is in the straight condition, as shown in FIG. 2A. Proximal end 122b of the second component 120 connects to the distal end 116a of inner tube 116 at connection point 126. Rotating the inner tube 116 around axis 101 rotates the second component 120 around axis 101.

Figure 6A:
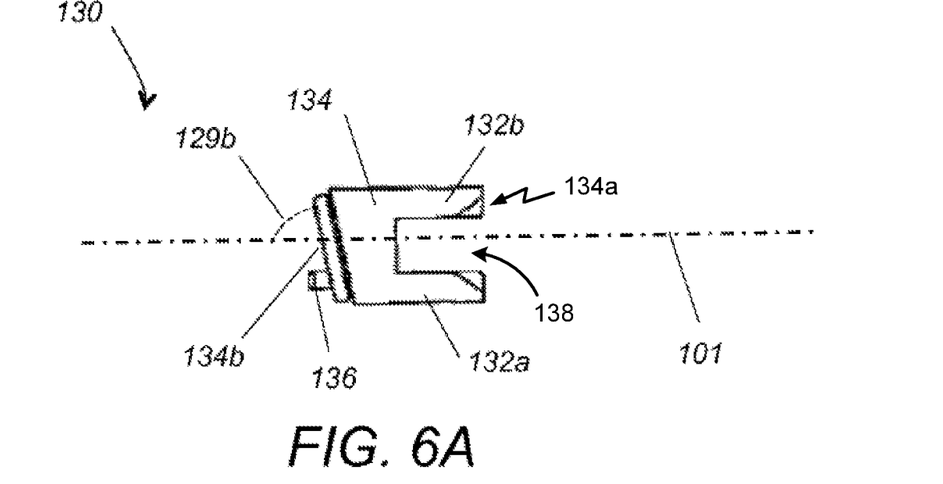
FIG. 6A is a side view of the third component of the articulating shaft of FIG. 1.
Figure 6B:
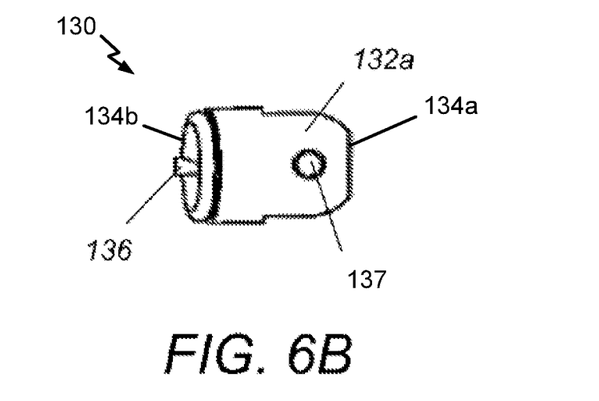
FIG. 6B is a bottom view of the third component of the articulating shaft of FIG. 1.
Figure 6C:
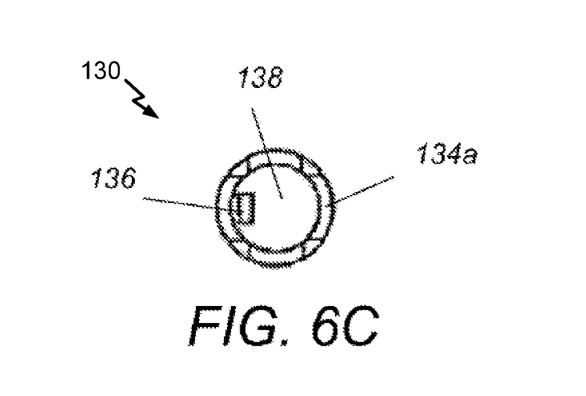
FIG. 6C is a front end view of the third component of the articulating shaft of FIG. 1.

Third component 130 is placed adjacent to second component 120 along axis 101, as shown in FIG. 2A. Third component 130 also includes a tubular body 134 that has a diameter equal to the diameter of the second component 120 and to the diameter of the first component 110, as shown in FIG. 1A and FIG. 6A. Tubular body 134 has a proximal end 134b and a distal end 134a. Proximal end 134b is cut at an angle 129b relative to axis 101, as shown in FIG. 6A. Angle 129b is supplementary to angle 129a of the second component 120, so that end plane 134b aligns with end plane 122a when the shaft is in the straight condition, as shown in FIG. 2A. Distal end 134a has two parallel protrusions 132a, 132b extending from end plane 134a and being oriented perpendicular to end plane 134a. A gap 138 resides between protrusions 132a, 132b. Protrusions 132a, 132b are used to connect to a removable distal end assembly (not shown). Protrusions 132a, 132b include openings 137 used to engage a pin or a hook of the distal end assembly (not shown). Third component 130 also includes a pin 136 extending from the proximal end 134b, as shown in FIG. 6A. Pin 136 aligns and engages an opening or a slot in pin 114a of first component 110 in order to provide a keyed joint between the third component 130 and the first component 110. This mechanical keying of the first and third components 110, 130 prevents mating except when they are positioned in a certain orientation and allows rotational movement of the third and first components 130, 110, respectively.

In operation, the three components 110, 120, 130 are assembled and aligned along axis 101 (straight condition), as shown in FIG. 2A. Next, the inner tube 116 is rotated relative to the outer tube 110 and thereby the second component 120 is rotated around axis 101, while the first and third components 110, 130 do not rotate. A rotational motion of 180 degrees of the second component 120, rotates the proximal end plane 122b of the second component 120 until it matches and becomes co-planar with distal end plane 118a of the first component 110, as shown in FIG. 2B. This motion also rotates distal end plane 122a of the second component until it matches and becomes co-planar with proximal end plane 134b of the third component 130. Overall the 180 degree rotational motion of the second component 120 results in placing the third component 130 along axis 102 which is oriented at an angle 103 relative to axis 101, as shown in FIG. 2B (articulated condition). This new orientation of the third component 130 places any distal end assembly that is attached to the third component at an angle 103 relative to the axis 101.

Several embodiments of the present invention have been described. Nevertheless, it will be understood that various modifications may be made without departing from the spirit and scope of the invention. Accordingly, other embodiments are within the scope of the following claims.

What is claimed is:

1. An articulating shaft system comprising:
    a straight elongated shaft comprising:
        an outer tubular component having a distal end surface that is not perpendicular to a main axis of the straight elongated shaft; and
        an inner tubular component positioned within the outer tubular component and being co-axial with the main axis;
    a first articulating component being co-axial with the main axis and positioned adjacent to the distal end surface of the outer tubular component, the first articulating component comprising:
        a proximal end surface that is not perpendicular to the main axis; and a distal end surface that is not perpendicular to the main axis;
wherein the first articulating component is connected to the inner tubular component such that rotation of the inner tubular component within the outer tubular component around the main axis produces rotational motion of the first articulating component; and
a second articulating component being co-axial with the main axis and positioned adjacent to the distal end surface of the first articulating component, the second articulating component comprising a proximal end surface that is not perpendicular to the main axis, wherein the second articulating component is:
adapted not to rotate relative to the inner tubular component and the outer tubular component when the first articulating component is rotated by the inner tubular component; and
adapted to transition via translational motion from being co-axial with the main axis when the distal end surface of the first articulating component is co-axial with the main axis to not being co-axial with the main axis when the distal end surface of the first articulating component is not co-axial with the main axis;
wherein the distal end surface of the outer tubular component and the proximal end surface of the first articulating component remain in contact when the first articulating component is rotated by the inner tubular component; and
wherein the distal end surface of the first articulating component and the proximal end surface of the second articulating component remain in contact when the first articulating component is rotated by the inner tubular component.

2. The system of claim 1, wherein rotation of the first articulating component around the main axis positions the first articulating component and the second articulating component at an angle relative to the main axis.

3. The system of claim 2, wherein the system is configured to hold rigidly the second articulating component at the angle relative to the main axis.

4. The system of claim 1, wherein:
the proximal end surface of the first articulating component is co-planar with the distal end surface of the outer tubular component; and
the distal end surface of the first articulating component is co-planar with the proximal end surface of the second articulating component.

5. The system of claim 1, wherein the outer tubular component further comprises at least one pin configured to connect the outer tubular component with the second articulating component.

6. The system of claim 5, wherein the second articulating component further comprises at least one pin configured to engage the at least one pin of the outer tubular component so as to provide a keyed joint between the outer tubular component and the second articulating component that prevents rotation of the second articulating component relative to the outer tubular component.

7. The system of claim 1, wherein the second articulating component is further configured to connect to a removable distal end assembly.

8. The system of claim 7, wherein the second articulating component further comprises two opposing protrusions configured to provide the connection to the removable distal end assembly.

9. The system of claim 8, wherein each of the two opposing protrusions includes at least one opening defined therein.

10. The system of claim 1, wherein an outer surface of the system is sealed such that it does not include any gaps.

11. The system of claim 1, wherein the outer tubular member, the first articulating component, and the second articulating component are of equal outer diameter.

12. A medical device comprising the system of claim 1.

13. The medical device of claim 12, wherein the medical device is a hand-held medical device.

14. The medical device of claim 12, wherein the straight elongated shaft is positioned proximal to a handle of the medical device.

15. A method for articulating a distal end assembly, the method comprising:
providing a straight elongated shaft comprising:
an outer tubular component having a distal end surface that is not perpendicular to a main axis of the straight elongated shaft; and
an inner tubular component positioned within the outer tubular component and being co-axial with the main axis;
providing a first articulating component being co-axial with the main axis and positioned adjacent to the distal end surface of the outer tubular component, the first articulating component comprising:
a proximal end surface that is not perpendicular to the main axis; and
a distal end surface that is not perpendicular to the main axis;
wherein the first articulating component is connected to the inner tubular component such that rotation of the inner tubular component within the outer tubular component around the main axis produces rotational motion of the first articulating component;
providing a second articulating component being co-axial with the main axis and positioned adjacent to the distal end surface of the first articulating component, the second articulating component comprising a proximal end surface that is not perpendicular to the main axis;
attaching a distal end surface of the second articulating component to a distal end assembly; and
rotating the first articulating component around the main axis such that the first articulating component, the second articulating component, and the distal end assembly are positioned at an angle relative to the main axis, wherein the second articulating component is:
adapted not to rotate relative to the inner tubular component and the outer tubular component when the first articulating component is rotated by the inner tubular component; and
adapted to transition via translational motion from being co-axial with the main axis when the distal end surface of the first articulating component is co-axial with the main axis to not being co-axial with the main axis when the distal end surface of the first articulating component is not co-axial with the main axis;
wherein the distal end surface of the outer tubular component and the proximal end surface of the first articulating component remain in contact when the first articulating component is rotated by the inner tubular component; and
wherein the distal end surface of the first articulating component and the proximal end surface of the second articulating component remain in contact when the first articulating component is rotated by the inner tubular component.

16. The method of claim 15, wherein the outer tubular component further comprises at least one pin configured to connect the outer tubular component with the second articulating component.

17. The method of claim 16, wherein the second articulating component further comprises at least one pin configured to engage the at least one pin of the outer tubular component so as to provide a keyed joint between the outer tubular component and the second articulating component that prevents rotation of the second articulating component relative to the outer tubular component.

18. The method of claim 15, wherein the second articulating component further comprises two opposing protrusions configured to provide the connection to the distal end assembly.

19. The method of claim 15, wherein:
the proximal end surface of the first articulating component is co-planar with the distal end surface of the outer tubular component; and
the distal end surface of the first articulating component is co-planar with the proximal end surface of the second articulating component.

20. The method of claim 15, wherein the first articulating component, the second articulating component, and the distal end assembly are configured to be held rigidly at the angle relative to the main axis.

* * * * *